(12) United States Patent
Anderson et al.

(10) Patent No.: US 10,487,323 B2
(45) Date of Patent: Nov. 26, 2019

(54) ONE-POT MULTIPLEX GENE SYNTHESIS

(71) Applicants: THE REGENTS OF THE UNIVERSITY OF CALIFORNIA, Oakland, CA (US); AGILENT TECHNOLOGIES, INC., Santa Clara, CA (US)

(72) Inventors: John Christopher Anderson, Berkeley, CA (US); Bo Curry, Santa Clara, CA (US); Timothy Hsiau, Berkeley, CA (US)

(73) Assignees: THE REGENTS OF THE UNIVERSITY OF CALIFORNIA, Oakland, CA (US); AGILENT TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 15/500,972

(22) PCT Filed: Aug. 3, 2015

(86) PCT No.: PCT/US2015/043469
§ 371 (c)(1),
(2) Date: Feb. 1, 2017

(87) PCT Pub. No.: WO2016/019387
PCT Pub. Date: Feb. 4, 2016

(65) Prior Publication Data
US 2017/0218358 A1    Aug. 3, 2017

Related U.S. Application Data

(60) Provisional application No. 62/032,420, filed on Aug. 1, 2014.

(51) Int. Cl.
C12N 15/10 (2006.01)
C12P 19/34 (2006.01)
C12Q 1/6874 (2018.01)
C12N 15/66 (2006.01)
B01J 19/00 (2006.01)

(52) U.S. Cl.
CPC ...... *C12N 15/1068* (2013.01); *B01J 19/0046* (2013.01); *C12N 15/1031* (2013.01); *C12N 15/66* (2013.01); *C12P 19/34* (2013.01); *C12Q 1/6874* (2013.01); *B01J 2219/00585* (2013.01); *B01J 2219/00722* (2013.01)

(58) Field of Classification Search
None
See application file for complete search history.

(56) References Cited

U.S. PATENT DOCUMENTS

2003/0138782 A1    7/2003  Evans
2013/0203606 A1    8/2013  Pollack et al.

OTHER PUBLICATIONS

Anderson and Schultz, Biochemistry, 43(32):9598-9608 (2003).
Lucks et al., Proc. Natl. Acad. Sci. U.S.A., 108(27):11063-11068 (2011).
Grote et al. Nucleic Acids Res., 33 (suppl. 2):W526-531 (2005).
Kosuri et al., Proc. Natl. Acad. Sci. U.S.A., 110(34):14024-14029 (2013).
Nakamura et al., Nucleic Acids Res., 28:292 (2000).
Schütze et al., Analytical Biochemistry, 410: 155-157 (2011).
Shagin et al., Nucleic Acids Research, 27(18): e23 (1999).
Williams et al., Nature Methods, 3: 545-550 (2006).

*Primary Examiner* — Channing S Mahatan
(74) *Attorney, Agent, or Firm* — Morgan, Lewis & Bockius LLP; Jeffry S. Mann; Todd Esker

(57) ABSTRACT

The present invention provides methods for generating a library of synthetic polynucleotides. The present invention also provides methods for generating proteins encoded by the library of synthetic polynucleotides. In addition, provided herein are methods for determining the soluble expression of said proteins. This invention is based, in part, on the discovery of a method for selecting optimal oligonucleotides in combination with performing a phosphorylation reaction, ligation reaction and PCR amplification in a single reaction vessel to produce synthetic polynucleotides in a multiplex manner.

40 Claims, 3 Drawing Sheets
Specification includes a Sequence Listing.

Figure 3 ered in the reaction vessel. The plurality of synthetic polynucleotides may encode a plurality of target proteins. In some instances, the plurality of target proteins is about 10 to about 200 target proteins.

ONE-POT MULTIPLEX GENE SYNTHESIS

CROSS-REFERENCE TO RELATED APPLICATIONS

This application is a 371 U.S. National Phase application of PCT International Application No. PCT/US2015/043469 filed Aug. 3, 2015 which claims the benefit under 35 U.S.C. § 119(e) of U.S. Provisional Application No. 62/032,420 filed on Aug. 1, 2014, both of which are incorporated herein by reference in their entireties for all purposes.

BACKGROUND OF THE INVENTION

Gene synthesis is a cornerstone of both the fields of pharmaceutical and synthetic biology. Unfortunately, the use of gene synthesis methods in industrial applications is limited by their high cost and low through-put. Conventional gene synthesis assembly methods generate errors that require clonal enzymatic correction or sequencing to select error-free assemblies. In addition, the methods have been difficult to scale-up and involve complicated protocols, some of which require the use of robotics. The current invention addresses the need to produce cost-effective and error-free gene synthesis assemblies.

BRIEF SUMMARY OF THE INVENTION

This invention is based, in part, on the discovery of a method for selecting optimal oligonucleotides in combination with performing a phosphorylation reaction, ligation reaction and PCR amplification in a single reaction vessel to produce synthetic polynucleotides in a multiplex manner. In some instances, the synthetic polynucleotides are about 800 bp or more. The method can be used to generate one or more synthetic polynucleotides that encode one or more target proteins. In addition, the synthetic polynucleotides can be expressed in host cells to generate a library of proteins.

Provided herein is a method for producing simultaneously a plurality of synthetic polynucleotides from a plurality of oligonucleotides such that the synthetic polynucleotide encodes a target protein. An exemplary method includes:
a) designing the plurality of oligonucleotides, wherein a codon of the oligonucleotide is selected based on the codon usage frequency of a host cell and an overhang region forms when the oligonucleotide anneals to another oligonucleotide in the plurality;
b) generating the plurality of oligonucleotides;
c) phosphorylating the plurality of oligonucleotides;
d) performing a ligation reaction with the plurality of phosphorylated oligonucleotides to generate a plurality of nucleic acid templates; and
e) performing a PCR reaction in a single reaction vessel to produce the plurality of synthetic polynucleotides.

In some embodiments, the synthetic polynucleotide is about 400 bp to about 1.5 kb. Alternatively, the synthetic polynucleotide is about 800 bp. In some embodiments, each synthetic polynucleotide of the plurality is the same length.

In some embodiments, at least about 10 different synthetic polynucleotides are produced in the reaction vessel. Alternatively, at least about 100 different synthetic polynucleotides are produced in the reaction vessel. The plurality of synthetic polynucleotides may encode a plurality of target proteins. In some instances, the plurality of target proteins is about 10 to about 200 target proteins.

In some embodiments, the method further comprises determining the nucleic acid sequences of the synthetic polynucleotides. In some instances, this is performed using next-generation sequencing.

In some instances, the codon usage frequency is the codon usage frequency of *Escherichia coli*. In some embodiments, the oligonucleotide has less than or equal to 15 nucleic acids at either the 5' end or 3' end that are identical to those of another oligonucleotide in the plurality.

The oligonucleotide may be at least about 30 bp to about 175 bp. In some embodiments, the oligonucleotide is at least about 100 bp to about 175 bp. Alternatively, the oligonucleotide may be about 175 bp or more.

In some embodiments, the step of generating the plurality of oligonucleotides comprises synthesizing the oligonucleotides on a microarray. The step of performing a PCR reaction may include performing emulsion PCR and suppression PCR. In some embodiments, emulsion PCR comprises an oil, a surfactant, a DNA polymerase, a buffer and dNTPs.

In some embodiments, the method further comprises isolating the synthetic polynucleotide. In some instances, the step of isolating the synthetic polynucleotide includes:
i) introducing the synthetic polynucleotide into an expression vector to generate an expression construct;
ii) introducing the expression construct into a host cell to produce a transformed host cell;
iii) culturing the transformed host cell under conditions to promote the expression of the expression construct; and
iv) extracting the synthetic polynucleotide from the transformed host cell.

In some embodiments, the synthetic polynucleotide may be operably linked to a detectable, selectable or screenable marker, such as, but not limited to, an essential metabolic gene, an antibiotic resistance gene, a toxic metal resistance gene, a cell surface protein and the like. The method may include culturing the transformed host cell under selective conditions and extracting the synthetic polynucleotide from the cell. Alternatively, the method includes screening the transformed host cell to enrich for a cell that expresses the synthetic polynucleotide and extracting the synthetic polynucleotide from the cell.

In some embodiments, the method further comprises producing a protein encoded by the synthetic polynucleotide. In some instances, the method includes:
i) introducing the synthetic polynucleotide into an expression vector to generate an expression construct;
ii) introducing the expression construct into a host cell to produce a transformed host cell;
iii) culturing the transformed cell under conditions to produce the protein encoded by the synthetic polynucleotide.

The method can also include isolating the protein produced by the transformed cell.

The expression construct may include the synthetic polynucleotide operably linked to an export signal gene and a beta-lactamase folding reporter, wherein the export signal gene is located at the 5' end of the synthetic polynucleotide and the beta-lactamase folding reporter is located at the 3'end of the synthetic polynucleotide. In one embodiment, the export signal gene is the Tat export signal gene derived trimethylamine N-oxide reductase. In some embodiments, the method further includes determining that the protein can be expressed as a soluble protein if the transformed host cell grows in the presence of ampicillin or a derivative thereof.

Also provided herein is a system for generating a plurality of synthetic polynucleotides in a multiplex manner using the method of described above. An exemplary system includes:
a) a module for designing oligonucleotides comprising an algorithm for selecting oligonucleotides, wherein a codon of the oligonucleotide is selected based on the codon usage frequency of a host cell and an overhang region forms when the oligonucleotide anneals to another oligonucleotide in the plurality;
b) a module for generating a plurality of oligonucleotides;
c) a module for synthesizing the plurality of synthetic polynucleotides in a multiplex manner comprising:
  i) reagents for phosphorylating the plurality of oligonucleotides;
  ii) reagents for ligating the phosphorylated oligonucleotides to generate the plurality of nucleic acid templates; and
  iii) reagents for amplifying the nucleic acid template in an emulsion to generate the plurality of synthetic polynucleotide.

In an exemplary embodiment, the reagents for amplifying the nucleic acid template are reagents for emulsion PCR and reagents for suppression PCR.

In some instances, the codon usage frequency is the codon usage frequency of *Escherichia coli*. In one embodiment, the algorithm selects oligonucleotides that are at least 100 bp long and have less than or equal to 15 nucleic acids at either the 5' end or 3' end that are identical to those of a selected oligonucleotide. For example, the oligonucleotides may be selected based on the uniqueness of their 3' ends (e.g., of the terminal 15 bp to 20 bp), wherein the uniqueness from 6 bp to 20 bp is determined according to the total number of oligonucleotides and the sequence complexity of the target genes. The algorithm may select oligonucleotides that have an overhang region with a melting temperature (Tm) of about 65° C.

The selected oligonucleotides may be at least about 30 bp to about 175 bp. In some embodiments, the selected oligonucleotides are at least about 100 bp to about 175 bp. Alternatively, the selected oligonucleotides may be about 175 bp or more. In one embodiment, the module for generating the plurality of oligonucleotides comprises a microarray.

In some embodiments, the synthetic polynucleotide of the plurality is about 400 bp to about 1.5 kb. Alternatively, the synthetic polynucleotide of the plurality is about 800 bp. In some embodiments, each synthetic polynucleotide of the plurality is the same length.

The reagents for phosphorylating may include a polynucleotide kinase and a buffer. The reagents for ligating may include a DNA ligase and an aqueous buffer. The reagents for amplifying may include an oil, a surfactant, a DNA polymerase, an aqueous buffer and dNTPs. In some embodiments, the module for synthesizing further comprises a reagent for isolating the plurality of synthetic polynucleotides.

Other objects, features, and advantages of the present invention will be apparent to one of skill in the art from the following detailed description and figures.

BRIEF DESCRIPTION OF THE DRAWINGS

FIG. 1A shows an exemplary design of a target gene and the designed oligonucleotides that span the target gene. The synthons do not exceed 950 bp in length, including the Universal Forward and Universe Reverse (UF and UR, respectively) sequences, the Specific Forward and Specific Reverse (SF and SR, respectively) sequences, the restriction endonuclease (RE) recognition sites, and filler (Fi) sequences. The oligonucleotdies are designed such that all terminal 15 nucleotides are unique. FIG. 1B shows an overview of the gene synthesis process. Oligonucleotides are phosphorylated and subjected to a high temperature ligation. Next, the synthetic genes can be amplified by either specific PCR or emulsion PCR and suppression PCR in a single reaction vessel and in a multiplex manner. FIG. 1C shows the expression of 88 synthetic GFP in cells. 1 mL of cells were grown overnight, concentrated by centrifugation and resuspended in PBS in a clear bottom 96-well plate with opaque siding. The images are combined from UV illumination and blue light illumination. Well F4 (marked with an X) contains empty media.

FIG. 2A shows a portion of the expression construct containing the Tat pathway secretion signal (ss-TorA), the synthetic gene (e.g., ORF), and the TEM-1 β-lactamase gene. Test ORFs were fused at the N-terminus to ssTorA and at the C-terminus to β-lactamase. FIG. 2B shows a method for determining if the target polypeptide (and synthetic polypeptide) is expressed as a soluble protein. ORFs encoding proteins with soluble expression export mature β-lactamase fusion proteins to the periplasm of the host cell (e.g., *E. coli*). The library is then selected on various ampicillin concentrations and relative abundances are assayed by Illumina MiSeq sequencing.

FIG. 3A shows a graph of normalized occurrence of six representative ORFs. FIG. 3B shows the growth phenotype of strains on plates with different amounts of ampicillin.

DETAILED DESCRIPTION OF THE INVENTION

I. Introduction

In one aspect, the invention is based, in part on the discovery, that synthetic polynucleotides (e.g., gene assemblies) can be generated in a multiplex manner in a single reaction vessel from a pool of pre-designed oligonucleotides. Accordingly, the invention provides methods and a system for generating the synthetic polynucleotides and a pool of proteins encoded by said polynucleotides.

Compared to conventional methods of gene synthesis, the method provided herein can generate synthetic polynucleotides that are about 800 bp or longer. In addition, the method allows for the generation of a library of unique synthetic polynucleotides in a single PCR amplification reaction. In an exemplary embodiment, the invention utilizes emulsion PCR of a plurality of phosphorylated polynucleotides, followed by suppression PCR of the product of the emulsion PCR to generate the plurality of synthetic polynucleotides.

In an exemplary embodiment, the invention provides a method using emulsion PCR to add inverted repeats to the ends of the amplicons that act as suppression tails. A single primer which binds to the inverted repeats is used in suppression PCR for amplification. The inverted repeats can anneal to each other and compete with primer binding. Shorter amplicons exhibit the suppression effect more than longer amplicons, thus suppression PCR is biased towards longer amplicons. In an exemplary embodiment, suppression PCR products are cloned directly into an expression vector. In various embodiments, colonies are randomly picked and sequenced.

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Molecular Cloning, A Laboratory Manual. (Sambrook, J. and Russell, D., eds.), CSHL Press, New York (3rd Ed, 2001); and Current Protocols in Molecular Biology. (Ausubel et al., eds.), New Jersey (1994-1999).

II. Definitions

As used herein, the following terms have the meanings ascribed to them unless specified otherwise.

The term "synthetic polynucleotide" refer to a chemically synthesized polynucleotide, respectively. For example, a synthetic polynucleotide (or a copy or complement of a synthetic polynucleotide) is one that has been manipulated using well known methods. In some instance, the synthetic polynucleotide includes an open reading frame or a protein-coding region.

The term "target protein" refers to a pre-selected amino acid sequence for a protein or a fragment thereof.

The term "reaction vessel" refers to a container or compartment used to contain the reagents of a reaction. Non-limiting examples of a reaction vessel include a microcentrifuge tube, PCR tube, well, microwell and droplet.

The term "phosphorylating" refers to introducing a terminal (5'-) phosphate group to an oligonucleotide.

The term "ligation reaction" refers the joining of nucleic acids together by catalyzing the formation of a phosphodiester bond. For instance, in a ligation reaction DNA ligase forms two covalent phosphodiester bonds between the 3' hydroxyl ends of one nucleotide with the 5' phosphate end of another.

The term "nucleic acid" or "polynucleotide" refers to a single or double-stranded polymer of deoxyribonucleotide or ribonucleotide bases read from the 5' to the 3' end. A nucleic acid will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see, e.g., Eckstein, F., Oligonucleotides and Analogues: A Practical Approach, Oxford University Press, 1991); and peptide nucleic acid backbones and linkages. Other analog nucleic acids include those with positive backbones; non-ionic backbones, and non-ribose backbones. Thus, nucleic acids or polynucleotides may also include modified nucleotides that permit correct read through by a polymerase. The terms "polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "codon usage frequency" refers to the frequency that specific codons are used more often than other synonymous codons during translation of genes in a particular organism. Codon usage frequencies can be tabulated using known methods (see, e.g., Nakamura et al., *Nucleic Acids Res.*, 28:292 (2000); Grote et al. *Nucleic Acids Res.*, 33 (suppl. 2):W526-531 (2005)). Codon usage frequency tables are also available in the art (e.g., in codon usage databases of the Department of Plant Genome Research, Kazusa DNA Research Institute, Japan). The method of generating a codon-optimized polynucleotide variant includes modifying one or more codons of a polynucleotide to eliminate codons that are rarely used in the host cell, and adjusting the AT/GC ratio to that of the host cell. Rare codons can be defined, e.g., by using a codon usage table derived from the sequenced genome of the host cell.

The term "complementary" refers to the ability of a nucleic acid in a polynucleotide to form a base pair with another nucleic acid in a second polynucleotide. For example, the sequence A-G-T is complementary to the sequence T-C-A. Complementarity can be partial, in which only some of the nucleic acids match according to base pairing, or complete, where all the nucleic acids match according to base pairing.

Optimal alignment of sequences for comparison may be conducted by the local homology algorithm of Smith and Waterman Add. *APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (CLUSTAL, GAP, BESTFIT, BLAST, FASTA, and TFASTA), or by inspection.

The term "percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. A "comparison window", as used herein, includes reference to a segment of any one of the number of contiguous positions, e.g., 20 to 600, usually about 50 to about 200, more usually about 100 to about 150 in which a sequence may be compared to a reference sequence of the same number of contiguous positions after the two sequences are optimally aligned.

The term "substantial identity" in the context of nucleic acid or amino acid sequences means that a polynucleotide or polypeptide comprises a sequence that has at least 50% sequence identity to a reference sequence, such as, but not limited to, the sequence of a target polynucleotide, a target polypeptide, a polynucleotide in a pool of polynucleotides or a polypeptide in a pool of polypeptides. Alternatively, percent identity can be any integer from 50% to 100%. Exemplary embodiments include at least: at least 25%, 30%, 35%, 40%, 45%, 50%, 55%, 60%, 65%, 70%, 75%, 80%, 85%, 90%, 95%, 99% or 100% identity compared to a reference sequence using the programs described herein; preferably BLAST using standard default parameters, as described below. For instance, two nucleic acid sequences or polypeptides are said to be "substantially identical" if the sequence of nucleotides or amino acid residues, respectively, in the two sequences is the same when aligned for maximum correspondence as described herein.

The phrase "a nucleic acid sequence encoding" refers to a nucleic acid which contains sequence information for a structural RNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform with codon preference in a specific host cell.

The terms "protein", "peptide" and "polypeptide" are used interchangeably and refer to an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An "expression construct" in the context of this invention refers to a nucleic acid construct, which when introduced into a host cell results in transcription and/or translation of a RNA or polypeptide, respectively. An expression cassette typically includes a nucleic acid sequence to be expressed, and other nucleic acid sequences necessary for expression of the sequence to be expressed. The nucleic acid sequence to be expressed can be a coding sequence or a non-coding sequence (e.g., an inhibitory sequence). Generally, an expression cassette is inserted into an expression vector (e.g., a plasmid) to be introduced into a host cell. An expression cassette can also include a nucleic acid encoding a protein operably linked to a promoter. The nucleic acid encoding a protein of interest is considered to be heterologous to a host cell, if the native (natural) host cells do not have the nucleic acid or protein of interest. An expression construct includes embodiments in which the nucleic acid is linked to an endogenous promoter, e.g., the nucleic acid may be integrated into the host cell's DNA such that expression is controlled by the native promoter. In further embodiments, the nucleic acid encoding the protein of interest is operably linked to a promoter that is introduced into the host cell along with the nucleic acid encoding the protein of interest. An expression cassette comprising a promoter operably linked to a second polynucleotide (e.g., a coding sequence) can include a promoter that is heterologous to the second polynucleotide as the result of human manipulation (e.g., by methods described in Sambrook et al., *Molecular Cloning-A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). An expression cassette (or expression vector) typically comprises polynucleotides in combinations that are not found in nature. For instance, human manipulated restriction sites or plasmid vector sequences can flank or separate the promoter from other sequences.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription. It is understood that limited modifications can be made without destroying the biological function of a regulatory element and that such limited modifications can result in regulatory elements of the host cell that have a substantially equivalent or enhanced function as compared to a wild-type regulatory element of the host cell. These modifications can be deliberate, as through site-directed mutagenesis, or can be accidental such as through mutation in hosts harboring the regulatory element as long as the ability to confer expression in the host cell is substantially retained.

The term "host cell" refers to a cell from any organism. Preferred host cells are derived from plants, bacteria, yeast, fungi, insects or other animals, including humans. Methods for introducing polynucleotide sequences into various types of host cells are well known in the art.

The terms "transfection" and "transformation" refer to introduction of a nucleic acid into a cell by non-viral or viral-based methods. The nucleic acid molecules may be gene sequences encoding complete proteins or functional portions thereof. See, e.g., Sambrook et al., 1989, *Molecular Cloning: A Laboratory Manual*, 18.1-18.88.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest.

The terms "culture," "culturing," "grow," "growing," "maintain," "maintaining," "expand," "expanding," etc., when referring to cell culture itself or the process of culturing, can be used interchangeably to mean that a cell is maintained outside its normal environment under controlled conditions, e.g., under conditions suitable for survival. Cultured cells are allowed to survive, and culturing can result in cell growth, stasis, differentiation or division. The term does not imply that all cells in the culture survive, grow, or divide, as some may naturally die or senesce. Cells are typically cultured in a liquid broth or on a solid media.

III. Synthetic Polynucleotides

Synthetic polynucleotides (e.g., gene synthesis assemblies) are known in the art. A synthetic polynucleotide can span the open reading frame of a target gene or a fragment thereof. For instance, two or more synthetic polynucleotides can be assembled (e.g., joined or ligated) together to encode a target protein.

In some embodiments, the synthetic polynucleotide can be about 400 bp to about 800 bp in length, e.g., 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, or 800 bp in length. In some instances, the synthetic polynucleotide is about 715 bp long. In other instances, the synthetic polynucleotide is about 800 bp long. Alternatively, the synthetic polynucleotide is longer than 800 bp, e.g., 825, 850, 875, 900, 925, 950, 1000, 1100, 1200, 1300, 1400, 1500, 1600, 1700, 1800, 1900, 2000 bp or longer. Optionally, the synthetic polynucleotide is shorter than 400 bp, e.g., 375, 350, 325, 300, 275, 250, 225, 200, 175, 150, 125, 100 bp or shorter.

The sequence of the synthetic polynucleotide encodes a preselected target protein or a fragment thereof. For instance, the target protein can be encoded by one or more unique synthetic polynucleotides, e.g., 1, 2, 3, 4, 5, 6, 7, 8, 9, 10 or more unique polynucleotides produced by the method described herein.

The method described herein can produce simultaneously at least 2 to about 100 or more synthetic polynucleotides, e.g., at least 2, 3, 4, 5, 6, 7, 8, 9, 10, 15, 20, 25, 30, 35, 40, 45, 50, 55, 60, 65, 70, 75, 80, 85, 90, 95, 100 or more unique synthetic polynucleotide. Alternatively, about 10 to about 100 unique synthetic polynucleotides, e.g., 10, 15, 20, 25, 30, 35, 40, 45, 50, 55, 60, 65, 70, 75, 80, 85, 90, 95, 100 unique synthetic polynucleotides are produced simultaneously. Optionally, about 100 to about 500 unique synthetic polynucleotides, e.g., about 100, 150, 200, 250, 300, 350, 400, 450, or 500 unique synthetic polynucleotides are produced simultaneously.

The method described herein can produce simultaneously at least 1 to about 100 target genes or fragments thereof, e.g., at least 1, 2, 3, 4, 5, 6, 7, 8, 9, 10, 15, 20, 25, 30, 35, 40, 45, 5, 55, 60, 65, 70, 75, 80, 85, 90, 95 or 100 target genes or fragments thereof.

IV. Selecting Oligonucleotides

A plurality of oligonucleotides are selected for each specific synthetic polynucleotide to be generated by the multiplex method, wherein more than one synthetic polynucleotide is made. The oligonucleotides can be computationally designed across all the synthetic polynucleotides. The algorithm can standardize the length of the preselected synthetic polynucleotides and computationally minimize sequence crosstalk. For length standardization, randomly selected padding sequences with a 50% GC content can be added to the 3' end of the synthetic polynucleotide such that all the synthetic polynucleotides of the pool are the same length. Based on the sequence of the synthetic polynucleotide, codons can be randomly chosen with a choice weight proportional to the codon frequencies for a host cell such as, but not limited to, bacteria, e.g., *Escherichia coli*, yeast, e.g., *Saccharomyces cerevisiae* and *Pichia Pastoris*, filamentous fungi, e.g., *Aspergullus, Trichoderma* and *Myceliophthora* thermophile, eukaryotic cells, plant cells and animal cells. For instance, the nucleic acid sequence of the synthetic polynucleotide is codon-optimized for a specific host cell. In some embodiments, the algorithm selects oligonucleotides that adhere to the following criteria: 1) are about 100 bp to about 250 bp, 2) can generate an overhang region with a melting temperature (Tm) of about 60° C.-70° C., and/or 3) have about 0 to about 20 nucleotides at either the 5' or 3' terminus that are identical with the nucleic acids at the 5' or 3' terminus of another oligonucleotide. Alternatively, the oligonucleotides selected by the algorithm: 1) are less than or equal to 175 bp, 2) have an overhang region with a Tm of 65° C., and 3) have less than or equal to 15 nucleotides at either the 5' or 3' terminus that are identical with the nucleic acids at the 5' or 3' terminus of another oligonucleotide. For example, the selected oligonucleotide may have up to about 15 nucleic acids at its 5' end that are not identical to the nucleic acids at the 5' end of another selected oligonucleotide.

The length of the selected oligonucleotides can be about 30 to about 200 nucleotides in length, e.g., about 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 nucleotides long. In one embodiment, the selected oligonucleotides are at least 100 nucleotides in length, e.g., 100, 105, 110, 115, 120, 125, 130, 135, 140, 145, 150, 155, 160, 165, 170, 175, 180, 185, 190, 195, 200 nucleotides or more. In another embodiment, the oligonucleotides are at least 175 nucleotides in length, e.g., 175, 176, 178, 179, 180, 181, 182, 183, 184, 185, 186, 187, 188, 189, 190, 191, 192, 193, 194, 195, 196, 197, 198, 199, 200 nucleotides or more. In some embodiments, the selected oligonucleotides is longer than 200 nucleotides, e.g., 210, 220, 230, 240, 250, 260, 270, 280, 290, 300, 310, 320, 330, 340, 350, 360, 370, 380, 390, 400 or more nucleotides.

As shown in FIG. 1A of the Examples, a series of oligonucleotides can be selected such that when they are annealed and ligated together, they span the sequence of the preselected synthetic polynucleotide. Thus, the pool of oligonucleotides can include at least two complementary oligonucleotides that generate overhang regions when annealed. For instance, a first oligonucleotide and a second, complementary oligonucleotide can be annealed together to make overhang regions (e.g., sticky ends).

In some embodiments, the complementary sequence is about 5 nucleotides to about 175 nucleotides or more in length, e.g., 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 nucleotides or more in length.

In some embodiments, no more than 15 nucleotides at the 5' end and at the 3' end of an oligonucleotide are identical to those of a different oligonucleotide in the pool. For instance, a first oligonucleotide has less than or equal to 15 nucleotides, e.g., 0, 1, 2, 3, 4, 5, 6, 7, 8, 9, 10, 11, 12, 13, 14, 15 nucleotides at its 5' terminus that are identical to those at the 5' terminus of a second oligonucleotide. Optionally, a first oligonucleotide in the pool has less than or equal to 15 nucleotides, e.g., 0, 1, 2, 3, 4, 5, 6, 7, 8, 9, 10, 11, 12, 13, 14, 15 nucleotides at its 3' terminus that is identical to those at the 3' terminus of a second oligonucleotide.

The oligonucleotides such as those corresponding to the terminal ends of the synthetic polynucleotide can include a restriction endonuclease recognition site sequence, a universal forward primer sequence, a universal reverse primer sequence, a gene-specific forward primer sequence, a gene-specific reverse primer sequence or any combination thereof. Non-limiting examples of universal forward primers are M13 Forward (-41) primer, M13 Forward (-20) primer, SP6 primer, T3 primer, T7 primer, and AUG1 Forward primer. Non-limiting examples of universal reverse primers are M13 Reverse (-41) primer, M13 Reverse (-20) primer T7 terminal reverse primer, and AUG1 Reverse primer. The universal primer sequence, e.g., forward or reverse primer sequence can be about 15 to about 25 nucleotides in length, e.g., about 15, 16, 17, 18, 19, 20, 21, 22, 23, 24, 25 nucleotides long. The gene-specific primer sequence, e.g., forward or reverse primer sequence, can be about 15 to about 25 nucleotides in length, e.g., about 15, 16, 17, 18, 19, 20, 21, 22, 23, 24, 25 nucleotides long.

V. Producing Oligonucleotides

The selected oligonucleotides can be synthesized on a multiplexed construction assembly, e.g., a oligonucleotide synthesis microarray to generate a pool (plurality) of oligonucleotides. Such oligonucleotide synthesis platforms are available from Agilent Technologies (Santa Clara, Calif.), Affymetrix (Santa Clara, Calif.), LC Sciences (Houston, Tex.), CustomArray (Bothell, Wash.), and the like. Alternatively, the oligonucleotides can be synthesized as a pool such as using microfluidics, microchips, and the like.

VI. Producing Synthetic Polynucleotides

The oligonucleotides can be 5' phosphorylated using standard methods known to one skilled in the art. For example, a 5' phosphorylation reaction typically contains oligonucleotides, a buffer containing ATP and DTT such as a T4 DNA ligase buffer, T4 polynucleotide kinase, and sterile water. In some embodiments, the reaction mixture is incubated at 37° C. for about 30 minutes to about 1 hour and heat inactivated at 65° C. for about 20 minutes to about 30 minutes.

The phosphorylated oligonucleotides can be ligated as a pool to form nucleic acid templates corresponding to the preselected synthetic polynucleotides. In some instance, the ligation reaction is a high temperature ligation reaction. The ligation reaction can include the phosphorylated oligonucleotides, polyethylene glycol (PEG) 3350 (e.g., Carbowax P146-3), a ligase, such as DNA ligase (e.g., 9° N™ ligase (New England Biolabs, Ipswich, Mass.), and a ligase buffer, such as DNA ligase buffer (e.g., 9° N™ ligase buffer). In some embodiments, the ligation reaction condition is 90° C.-98° C. for about 1-5 minutes, 65° C. for about 24 hours or less. The ligation reaction may be performed under conditions suitable for the generation of nucleic acid templates from the phosphorylated oligonucleotides.

Multiplexed emulsion PCR can be performed to generate the pool of synthetic polynucleotides. The ligation products generated from the ligation reaction serve as the nucleic acid templates in the emulsion PCR, thereby producing preselected synthetic polynucleotides.

To bias the amplification to long (>200 bp) PCR products, emulsion PCR and suppression PCR can be performed. To accomplish this, inverted repeat sequences can be added to the 5' and 3' ends of the PCR products during emulsion PCR. In some embodiments, the emulsion PCR primers contain sequences of inverted repeats. The emulsified PCR products can serve as the nucleic acid templates for suppression PCR.

Detailed descriptions of suppression PCR are found in, e.g., U.S. Pat. No. 5,565,340 and Siebert et al., *Nucleic Acids Res.*, 23(6):1087-1088 (1995). Briefly, the inverted repeat sequences function as suppression tails by competing with the suppression PCR primer for complementary binding. The inverted repeats tend to anneal each other, thereby preventing PCR primer binding. Since shorter amplicons undergo inverted repeat annealing more often than longer amplicons, the suppression PCR favors generating long amplicons.

Emulsion PCR is a PCR amplification method performed in a water-in-oil emulsion. It is useful for enabling multiplexing. Detailed descriptions of emulsion PCR protocols are found in, e.g., Williams et al., Nature Methods, 3: 545-550 (2006) and Schütze et al., Analytical Biochemistry, 410: 155-157 (2011).

The oil mixture of the emulsion may contain an oil and a surfactant. Non-limiting examples of an oil include mineral oil, silicone based oil and fluorinated oil. Non-limiting examples of a surfactant useful in the present invention include a silicone surfactant, a fluorinated surfactant, and a non-ionic surfactant such as sorbitan monooleate (e.g., Span™ 80, Innovadex, Overland Park, Kans.), polyoxyethylenesorbitsan monooleate (e.g., Tween™ 80), dimethicone copolyol (e.g., Abil® EM90), polysiloxane, polyalkyl polyether copolymer, polyglycerol esters, poloxamers, PVP/hexadecane copolymers (e.g., Unimer U-151), a high molecular weight silicone polyether in cyclopentasiloxane (e.g., DC 5225C, Dow Corning, Midland, Mich.). In some embodiments, the oil mixture contains one or more surfactants and an oil. For instance, the oil mixture may include Span™ 80, Tween™ 80, Triton X-100 and mineral oil.

In some embodiments the PCR mixture (e.g., the water mixture) includes the pool of ligated products, emulsion PCR primers, a DNA polymerase (e.g., Q5® High-Fidelity DNA polymerase, New England Biolabs, Ipswich, Mass.), a compatible DNA polymerase reaction buffer, dNTPS, and sterile water. In some instance, the PCR mixture includes universal primers, gene-specific primers or a combination thereof.

To generate the emulsion, the PCR mixture can be mixed with the oil mixture at a 1:10 (PCR:oil) volumetric ratio. For example, the PCR mixture is added in a dropwise manner to the oil mixture. Typically, a water-in-oil emulsion PCR mixture can generated about $10^8$-$10^9$ PCR compartments per mL of the emulsion. The emulsified PCR reactions can be pipeted as aliquots into a PCR plate which then undergoes PCR thermocycling. The emulsified PCR reactions may be pipeted as droplets using a droplet generator or other microfluidic technologies.

To break the emulsion, the emulsified PCR products may be combined together into a microcentrifuge tube and centrifuged to the oil and aqueous phases. The oil phase is then removed and discharged. An organic solvent such as, but not limited to, isobutanol or water-saturated diethyl ether, can be added to break the emulsion. Generally, the solvent is added to the pooled PCR reaction and then the microcentrifuge tube is vortexed. The solvent phase is then discarded.

In some instances, the PCR products that include the synthetic polynucleotides are cleaned using a bead or a column. Useful columns include PCR clean-up columns (Zymo Research), Wizard SV Gel and PCR Clean-Up System).

Suppression PCR can be performed using a single primer that can amplify one or more of the preselected synthetic polynucleotides present in the pool of PCR products. In some embodiments, the primer binds to a region at the 5' terminus or 3' terminus of the synthetic polynucleotide. Detailed descriptions of suppression PCR are found in, e.g., Shagin et al., Nucleic Acids Research, 27(18): e23 (1999).

The synthetic polynucleotides can be analyzed using standard techniques known to those skilled in the art, such as, but not limited to, gel electrophoresis, sequencing (e.g., Sanger method or next-generation sequencing), restriction enzyme digestion analysis, and the like.

In some embodiments, when a target gene corresponds to more than one unique synthetic polynucleotide, standard recombinant biology techniques, such as restriction enzyme digestion and ligation, are used to assemble the synthetic polynucleotides to form the target gene.

The synthetic polynucleotides can be cloned into an expression vector and then stably expressed in a host cell. The transformed host cell can be used to generate proteins encoded by the synthetic polynucleotides. Detailed description of standard recombinant biology methods are found in, e.g., Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998).

VII. Generating Proteins Encoded by Synthetic Polynucleotides

A variety of methods for expressing proteins from a polynucleotide are known. In some embodiments, the synthetic polynucleotide described above can be cloned into an expression vector that is useful for expressing proteins in a host cell. For instance, the expression vector can include a tag (e.g., FLAG, 6×His tag, glutathione-S-transferase tag, cleavable tag, affinity tag, solubility tag), a selectable marker (e.g., antibiotic resistance gene), detectable marker (e.g., fluorescent marker) and/or a protein folding reporter (e.g., Tat export signal and beta-lactamase gene). In some embodiments, the expression vector is any vector useful for expressing proteins in a host cell. In other embodiments, the vector contains a selectable or screenable marker gene. The expression construct can be introduced (e.g., transformed, transfected or electroporated) into a host cell. The transformed cells can be cultured in selection media (e.g., broth or media containing an antibiotic). Alternatively, the transformed cells can be screened to identify those cells that express the synthetic polynucleotide. In some embodiments, the expression of the protein can be determined based on the growth of the transformed cells. The synthetic polynucleotide can be extracted from the cell using standard DNA extraction methods. The protein encoded by the synthetic polynucleotide can be isolated using standard protein extraction methods.

In some embodiments, the multiplexed synthetic polynucleotides are cloned into the expression vector in a multiplex manner to generate a library of expression constructs. The purified, multiplex synthetic polynucleotides can be digested with one or more restriction enzymes and then ligated to an expression vector containing the corresponding restriction enzyme recognition site(s). The library of constructs can be introduced into the host cells to make a library of transformants which can produce a library of proteins. In some instances, the transformed cells are plated onto solid media such that each colony represents one expression construct containing a single synthetic polynucleotide.

VIII. Screening for Expressing of Soluble Proteins

The soluble expression of a protein encoded by the preselected synthetic polynucleotide can be determined by using an expression vector containing a protein folding reporter, such as the pSALect vector or a derivative thereof. The pSALect vector which contains the Tat export signal sequence and a beta-lactamase folding reporter can be used to assay whether the synthetic polynucleotide encodes a soluble protein. In some embodiments, an expression construct containing the synthetic polynucleotide fused between the Tat signal sequence at the 5' end and the mature TEM-1 beta-lactamase sequence at the 3' end is cloned and transformed into *E. coli*. The transformed cells are grown on a media supplemented with ampicillin. The soluble expression of the protein can be assessed based on the growth of the cells. For instance, transformed cells that grow on media with ampicillin (e.g., 5 µg/ml to 100 µg/ml ampicillin) are determined to express a soluble protein encoded by the synthetic polynucleotide.

IX. Examples

Example 1

The following examples are offered to illustrate, but not to limit, the claimed invention.

This example illustrates a multiplex method for generating synthetic genes (e.g., gene synthesis assemblies) from oligonucleotides synthesized on a microarray platform. The example shows that the method was performed in a single reaction vessel. In addition, the example illustrates a method for producing synthetic proteins encoded by the synthetic polynucleotides. Furthermore, the example also illustrates the use of an expression assay for determining the soluble expression of such synthetic proteins.

Abstract

Our ability to engineer organisms with new biosynthetic pathways and genetic circuits is limited by the availability of protein characterization data. One critical piece of information is whether or not a gene will express in the recipient organism. With new tools for reading and writing DNA, there are opportunities for scalable assays that more efficiently mine this information. To that end, we have developed Multiplex Ortholog Library Synthesis and Expression Testing (MOLSET) for rapid building and expression characterization of many genes as a pool. This methodology enables the production of libraries of genes from microarray oligonucleotide pools without the need for robotics. The genes are then characterized as a pool using a genetic reporter for protein expression with a deep sequencing readout. Herein we demonstrate the feasibility of this approach by building and testing 90 genes for empirical evidence of soluble expression.

Introduction

The process of synthetic biology can be subdivided into three phases: the characterization of genes for function and the electronic encapsulation of this knowledge, forward design of multi-gene systems based on the encapsulated knowledge, and optimization of the organisms for real-world deployment. Recently, a design tool called the Act Synthesizer was developed to formalize the second phase. The Act Synthesizer uses a database of gene function information to compute the list of enzymatically reachable compounds and all potential routes to these compounds. Additionally, Act incorporates knowledge about host expression to rank these pathways for feasibility. The scope and quality of these predictions is dependent on raw observations of molecular function for a large number of gene products. Traditionally, information about protein expression in a non-native host has been performed on a small scale in a case-by-case manner. Though databases such as BRENDA have curated such knowledge in a consolidated human-readable format, the amount of data only partially covers the enzymes in the database. The scarcity of information limits the ability to prioritize biosynthetic targets and avoid common modes of design failure.

To address these limitations, the Multiplex Ortholog Library Synthesis and Expression Testing (MOLSET) was developed. This high-throughput, gene synthesis and expression assay method can assemble preselected genes generated from oligonucleotides and then test whether the gene encode proteins that have soluble expression in a host cell such as E. coli. In a multiplex manner, MOLSET designs oligos for assembly of up to a hundred genes from microarray oligonucleotides. The soluble expression of proteins encoded by the synthesized genes are assayed by using a recently-developed indirect folding reporter in conjunction with next-generation sequencing.

Existing strategies for gene synthesis assembly using microarray-derived oligonucleotides have been highly successful and deployed industrially [5, 6]. However, previous approaches have been difficult to scale and not widely accessible because 1) they use complicated protocols, 2) they require the use of robotics to be practical, and 3) they generate errors that require clonal enzymatic correction or sequencing to select correct clones. The advantages of this method are that the gene synthesis assembly reactions can be performed in a single reaction vessel (e.g., a standard microcentrifuge tube or microwell). The study described herein shows that the method was able to assemble the majority (>95%) of the preselected genes.

Results

A Robust Method for Ortholog Library Synthesis

Figure 1:
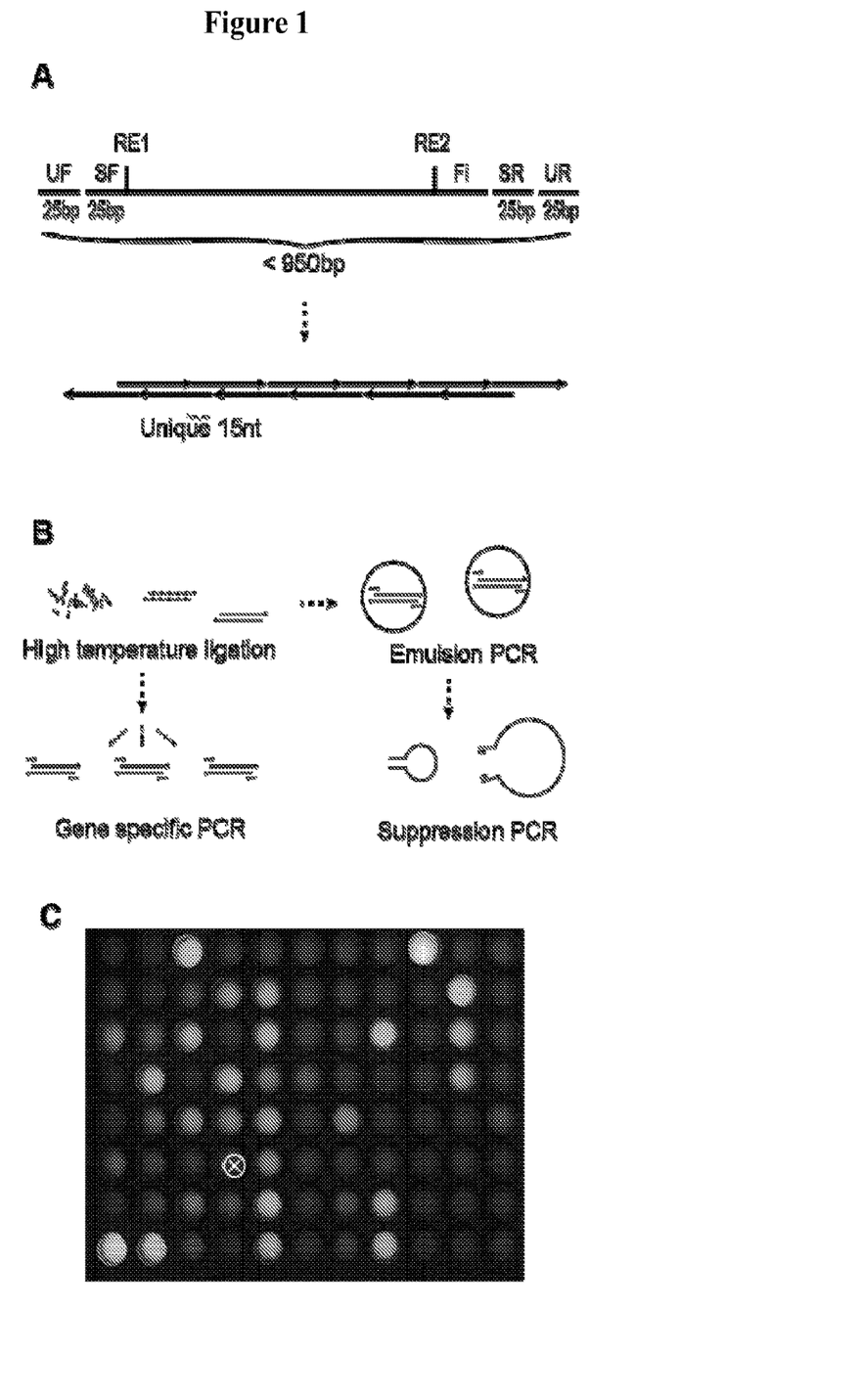
FIG. 1 shows an exemplary embodiment of the method for generating multiple genes in a single reaction vessel. The method is also referred to as Multiplex Ortholog Library Synthesis.

To enable multiplex ortholog library synthesis, we first standardized the length of synthesized sequences (synthons) and computationally minimized sequence crosstalk. For each design, synthon lengths were standardized by addition of random padding sequences (at the 3' end) (GC 50%). Codons were randomly chosen with a choice weight proportional to E. coli codon frequencies and oligonucleotides were designed to have no more than 15 nt in common at either end. Synthons for each gene were designed to be 711 bp. Gene-specific primer sequences and universal primer sequences were then added on the ends of synthon [6, 7, 16]. The sequence and oligonucleotide design constraints are illustrated in FIG. 1.

To empirically test if we could directly synthesize (assemble) genes from OLS pools, we designed a chip for 83 GFP family members for a total of 2,700 oligonucleotides and 60.6 kb of designed sequence. Oligonucleotides were synthesized by Agilent and received as a multiplex pool. After phosphorylation and a one-pot ligation, we performed gene-specific PCRs with orthogonal primer pairs and subcloned products into an expression vector. The robustness of the protocol was demonstrated when correctly-sized PCR products were observed even when 1 picomole of a 25 nt random oligonucleotide ($N_{25}$) was doped into the ligation reaction.

Correct gene assembly products for 80 genes were found by screening cloned products by clonal sequencing. The frequency of correct colonies determined by sequencing naive clones was determined to be 15% (6/40), with the majority of errors being point deletions, as is expected from the oligonucleotide synthesis methodology [8]. We next tested designs with more genes or longer synthons; however, we were unable to successfully concurrently assemble a large enough portion of the 1000 genes of 800 bp (unable to get any perfect sequences for a majority of genes) or 200 genes of 1.5 kb (only partial fragments were recovered). Thus we continued with the proven design of a 100 synthons of 800-900 bp in length.

Multiplex Ortholog Synthesis

A one-pot (e.g., one reaction vessel) process was investigated, eliminating the need for post assembly gene-specific amplification. Initial attempts to directly amplify the pool of assembled genes using universal PCR primers from the complex ligation assembly reaction using conventional PCR yielded only short (100-200 bp) products. We reasoned that the shorter products were favored by the PCR reaction and sought to counter or invert the length bias of PCR. We tried amplification by emulsion PCR [9] and suppression PCR [10]. Water-in-oil emulsion PCR was carried out on the ligation reaction and was able to generate a faint band of the correct size. Use of emulsion PCR alone was found not to be robust as sometimes no product was seen after amplification. We then used emulsion PCR to add inverted repeats to the ends of the amplicons that act as suppression tails. A single primer which binds to the inverted repeats is used in suppression PCR for amplification. The inverted repeats can anneal to each other and compete with primer binding [10]. Shorter amplicons exhibit the suppression effect more than longer amplicons, thus suppression PCR is biased towards longer amplicons. Suppression PCR products were then cloned directly into an expression vector and colonies were randomly picked and sequenced. The number of correct, full-length genes was 21% (3/14); however, 43% (6/14) of clones were fusions of two genes and the remainder of the errors were deletions or truncated genes. We concluded that Multiplex Ortholog Synthesis was sufficient to quickly create a multiplex pool of genes with an acceptable error rate, and next sought an appropriate downstream assay for expression of the assembled genes.

A High-Throughput Expression Assay Based on Tat Quality Control

Figure 2:
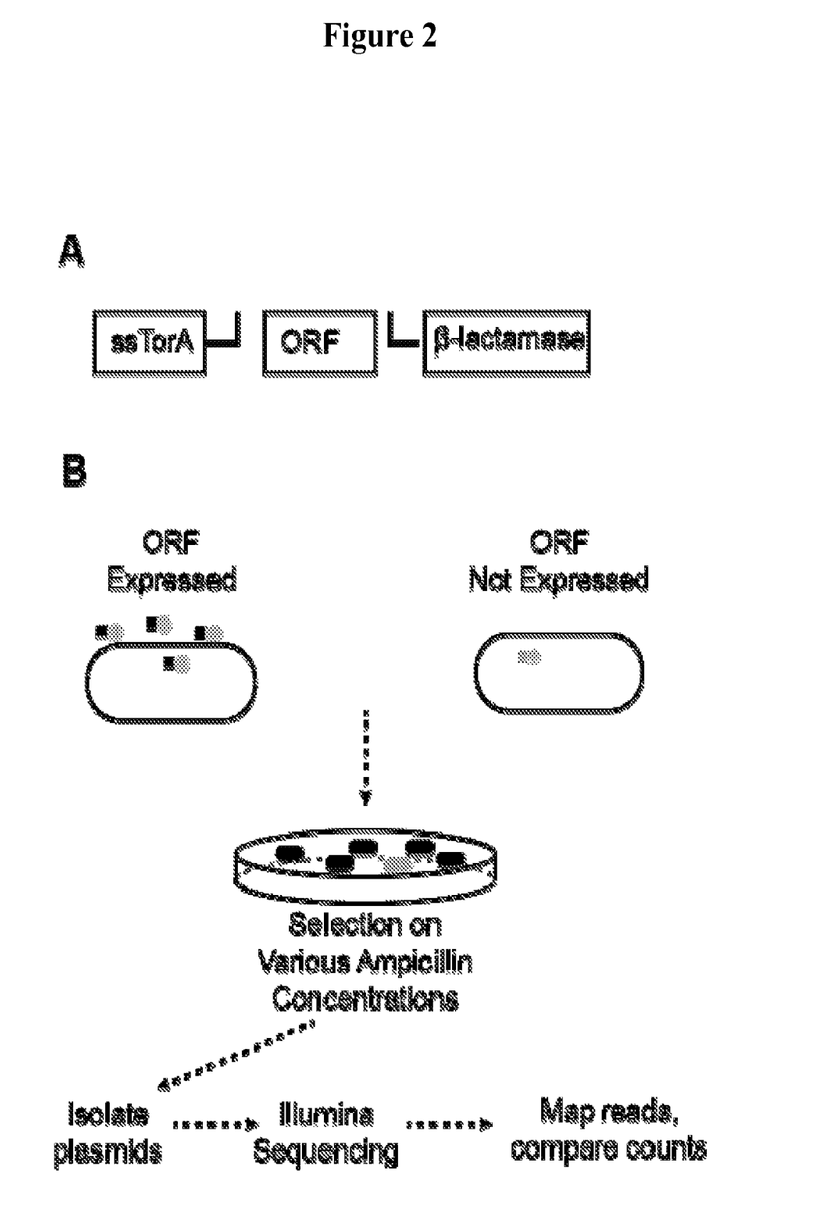
FIG. 2 shows a schematic overview of multiplex expression testing.

We sought to develop a multiplex expression assay in order to avoid individual cloning and sequence verification to select for correct genes. Recently, a selection assay based on the twin-arginine export quality control mechanism has been developed [11]. In this system, the gene of interest (GOI) is fused at the 5' end with a Tat export signal derived from trimethylamine N-oxide reductase (ssTorA) and fused at the 3' end with the mature TEM-1 beta-lactamase. Previous work has shown that translocation of the fusion protein and conferral of a resistance to ampicillin depends on the correct folding of the gene of interest [12]. We adapted this system in conjunction with next generation sequencing to develop our expression assay, as shown in FIG. 2.

We then designed a Multiplex Ortholog Library Synthesis pool for 95 genes, with 7 genes being negative controls previously shown to be poorly expressed in E. coli, 6 positive E. coli gene control, 1 engineered monomeric GFP also as a positive control, and 69 genes randomly chosen from the Act Ontology to represent a wide range of protein function to assess the performance of the multiplex expression assay. These genes were synthesized and cloned into the pSALect-EB vector. The plasmids with the assembled genes were transformed into E. coli by electroporation and a diversity of $5 \times 10^5$ was observed by titer plating Cells were plated on media supplemented with 1, 2.5, 5, or 10 μg/mL of ampicillin and chloramphenicol and found that 1 μg/mL of ampicillin yielded no drop in titer compared to chloramphenicol only. In contrast, we observed a 10% survival in titer on 2.5 or 5 μg/mL of ampicillin, which was comparable to the expected survival rate based on Sanger sequencing of naive clones. By sequencing clones grown from the 5 µg/mL ampicillin plate, we observed that 60% (27/45) were full length and correct, suggesting that the Multiplex Expression Assay system can also be used for multiplexed, non-enzymatic gene synthesis (assembly) error correction.

We next sought to characterize in a multiplex manner the expression of the synthesized genes and plated approximately $10^8$ cells on solid media supplemented with 5, 10, 50, or 100 µg/mL of ampicillin and 25 µg/mL of chloramphenicol. Plates were incubated at 30° C. overnight and we observed a titer of 10% for 5 µg/mL, 3% for 10 µg/mL, 1% for 50 µg/mL, and 0.3% for 100 µg/mL. Then, plates were scraped, mini-prepped to recover the plasmid library. Samples were prepared for sequencing using a TruSeq kit, and sequenced on a MiSeq. A total of 7.9 million reads were generated and mapped to the reference genes. Overall, 18.7% of reads were successfully mapped to a designed gene, with the minimal per-pool mapping rate of 17.6% and the maximal mapping rate of 20.2%.

The TruSeq random fragmentation method results in shotgun coverage of the plasmids and thus the full insert is not sequenced in any single read. Amplicon-based approaches would theoretically give rise to skewed counts as the inserts are of different sizes in our assay. Accordingly, partial gene fragments show up in our mapping. However, from the differences in the base-by-base coverage we can detect if coverage count arises from subfragments. By taking the median of the base-by-base coverage, we have a length-normalized count of representation. For the 5 µg/mL condition, the median read count correlated with Sanger sequencing data. The same gene, BRENDA92, was found to be the most represented in both the Sanger and the Illumina sequencing. Ratios between the most represented and the second ranked genes were comparable (8:3 clones with Sanger sequencing versus 3197:1131 using Illumina median read coverage). We then normalized counts by the pool to arrive at a dimensionless number that can be compared across different ampicillin conditions.

Our data showed that we synthesized 96% of the preselected genes. Expression was then computed by taking the pool-normalized values for each gene and normalizing to the 5 µg/mL condition. We found that all of the negative solubility controls exhibited a pattern of low representation in the higher ampicillin concentrations, rapidly falling off after 5 µg/mL. Of the GFP family members, we included a well-folding, monomeric positive control, mKG [13], and found that it was one of the most represented genes in the 100 µg/mL pool. Of the 6 *E. coli* positive controls, we found that two survived at high ampicillin concentrations, while the other 4 died at 50 µg/mL or more of ampicillin. These results suggest that while multiplex expression assaying using the tripartite fusion system is convenient with no observed false positives, it can generate false negatives.

Correlation with Confirmatory Experiments

Figure 3:
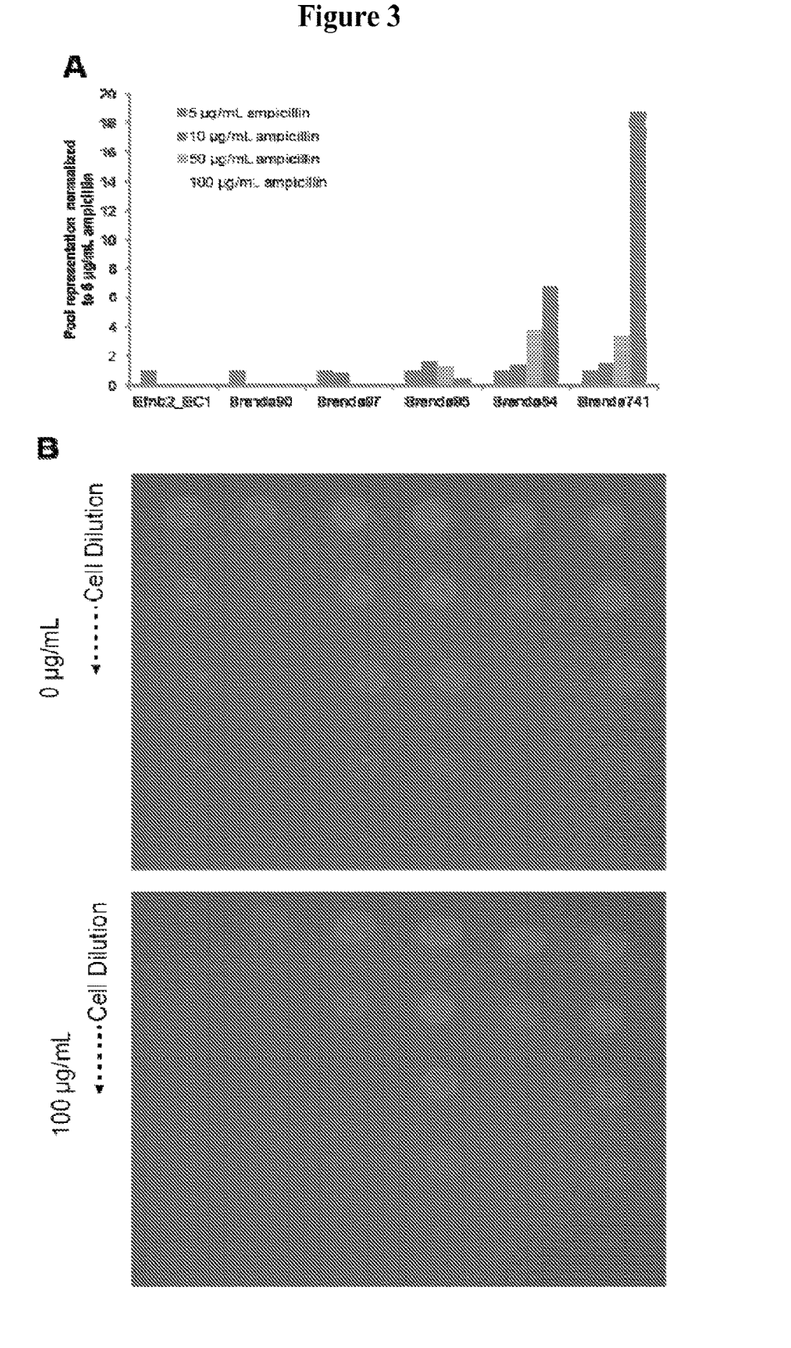
FIG. 3 shows that multiplex sequencing correlates with plate expression phenotypes.

In order to confirm the sequencing results from the expression experiment, we dilution spotted overnight cultures of 6 retransformed clones onto plates of 0-400 µg/mL of ampicillin to confirm the phenotypes. The dilution plating agreed with the NGS findings (FIG. 3). To independently confirm the expression of the 6 representative samples, we expressed them as FLAG-tagged chimeras and performed Western blotting to look at soluble versus insoluble fractions. The Western blot generally correlated with ampicillin growth but there was one exception, a dimer which expressed solubly as a FLAG-tag fusion (BRENDA90 in FIG. 3), again suggesting that the multiplex expression system can generate false negatives.

Uploading Expression Observations to the Act Ontology

NGS-predicted expression was then correlated with text mined expression predictions in the Act Ontology. Evidence for expression was inferred from the "Cloned" commentary section of the BRENDA database. We then searched for comments with the organism name "escherichia", and without the terms "inclusion bodies" and "folding", as evidence of expression. Of the 69 BRENDA-derived test genes, 58 (84%) were predicted by text mining to be expressed in *E. coli*. NGS predictions using a 10% representation cutoff (gene pool representation should be more than 10% of the pool representation observed in the 5 µg/mL condition) predicted 43 (62%) genes to be expressable.

Discussion

We have developed new methodology, called MOLSET, for rapidly building genes and characterizing their soluble expression. We simplified the process of fabricating genes from complex microarray oligonucleotide pools. Our method requires only one-pot reactions and is able to create genes with length 811 bp at the hundred-scale with a high rate of success (>95% of genes). These results enable researchers to perform only 5-steps to make a pool of 100 genes as opposed to hundreds of steps required by previous protocols. Additionally, with the use of the beta-lactamase fusion system and selecting on ampicillin, we have shown it is possible to perform non-enzymatic gene synthesis error reduction in a pooled format. Taking these steps in combination, even if the eventual goal is to generate clonal inserts, these methods could save researchers much labor.

Our motivation in developing the expression testing in MOLSET was the observation that expression issues greatly complicate genetic engineering projects and a way is needed to rapidly assess the feasibility of projects. Experienced researchers empirically learn patterns in the relationship between expression and classes of enzymes and avoid certain designs. For example, it is widely observed that P450 enzymes will not express in *E. coli* and this learned pattern is taken into account when choosing the chassis for a pathway that involves such an enzyme. However, the documented data on gene expression is sparse with few curated observations in public databases. Additionally, amongst a set of orthologs, some variants will express while others will not. For example, of six leucyl-tRNA synthetases cloned from archeal genomes, three express in *E. coli* (Anderson and Schultz, *Biochemistry*, 2003, 43(32):9598-9608). When researchers are only aware of one instance of a class that fails to express, they may incorrectly assume that the design cannot be instantiated. The lack of extensive characterization data leads researchers to expend resources on designs that cannot work, and miss opportunities due to false perceptions that a design will not work. With more cost effective and scalable means of surveying this information, design decisions can be made more precisely and reliably earlier in the planning process. Indeed, we show that by incorporating this mined data into an information system, we can computationally encapsulate the knowledge and automatically propagate it into design rankings.

Our multiplex expression test uses the Tat export pathway and a beta-lactamase folding reporter in conjunction with next-generation sequencing to quickly assay expressability of hundreds of genes using simple plate-based selections. Using the Tat export pathway allows our expression system to avoid false positives arising from translation due to spurious ribosomal binding sites internal to the assayed ORF; however, it also confers some disadvantages on our system. The Tat pathway has a limit on the size of proteins it can export, and while proteins of up to 120 kDa have been shown to be exported [12], the full scope of factors that influence what can and cannot be exported are unknown. Taken together, our findings suggest that the Tat β-lactamase system has few false positives, and a false negative rate that can be complemented by other approaches. Complementary approaches could either use a different method of fusing GOIs to the β-lactamase reporter or employ different reporters. There exists a loop insertion system developed for beta lactamase [22]. Also, GFP fusions are used as expression reporters and the results correlate with the solubility of the fusion partner [18]. There are also split or circular permutation GFP folding assays which only require a short 15 amino acids tag [19-21]. In conjunction with fluorescence-activated cell sorting and DNA sequencing, multiplexed expression assays could be performed with a broad range of organisms and genes. It is likely that all of these techniques have their own biases and caveats. A gene may appear to express in one assay and not another. Ideally, different reporter systems would be run in parallel and the discrepancies dealt with statistically in the design ranking process.

This methodology joins a suite of technologies that employ Next-Gen Sequencing as an analytical tool to map functional information to genetic 'parts'. Existing strategies include methods for mapping out the secondary structure of an RNA (Lucks et al., *Proc. Natl. Acad. Sci. U.S.A.*, 2011, 108(27):11063-11068), characterizing promoter strength of promoters and ribosome binding sites (Kosuri et al., *Proc. Natl. Acad. Sci. U.S.A.*, 2013, 110(34):14024-14029). Our study extends on those results and shows that it is possible to use NGS to read out soluble expression measurements. Expression is a necessary prerequisite for any further characterization of a gene product's molecular function. Thus, this methodology not only provides information for prioritizing designs but is also a practical first step in any effort for mining enzyme substrate specificity, protein:protein interactions, protein:DNA specificity, and the like. Additionally, the acquisition of large volumes of expression data will be useful for constructing models of translation such that ultimately this property of a gene can be predicted computationally.

Methods

Design of Synthesized Sequences

Sequences of all GFP family members in Uniprot were downloaded and a phylogenetic tree was made. We then selected GFP family members to synthesize from this tree. Protein sequences were converted to nucleotides using a weighted random codon algorithm designed in-house. Oligonucleotides were subsequently designed from the nucleotide sequences with the following constraints: no longer than 175 nt, overlaps Tm matched to 65° C., with no more than a 15 nt exact match between two oligonucleotides at either terminus.

Gene Synthesis by High-Temperature Ligation

Oligonucleotides were synthesized by Agilent and were received resuspended in 100 μL of TE buffer. Oligonucleotides were phosphorylated using 3 μL T4 Ligase Buffer (NEB), 24 μL OLS oligonucleotides, and 3 μL T4 PNK (NEB) at 37° C. for 1 hour. The reaction was heat inactivated at 65° C. for 30 min and held at 16° C. Testing several commercially available thermostable ligases revealed no differences in the gene-specific PCR for a subset of 20 genes. Whole pool ligation was performed with 12 μL phosphorylated oligonucleotides, 4 μL 50% 3350 PEG (Carbowax P146-3), 2 μL 9° N™ buffer, 2 μL (80 U) of 9° N™ ligase (NEB). Reactions were performed in a MJ Research PTC-200 thermocycler using the following program: 95° C. for 2 minutes, 65° C. for 24 hours, and 4° C. hold. The ligation product was used as template for gene-specific PCRs or emulsion PCR, described in next section. Gene-specific PCR was performed using 0.25 μL of the ligation product as template with gene-specific primers.

Emulsion PCR for Post-Ligation Amplification

Emulsion oil mix was prepared with 450 μL Span 80 (Fluka 85548), 40 μL Tween 80 (Sigma P4780), 5 μL Triton X-100 (Promega H5142), and 9505 μL mineral oil (Sigma M5904) as described in [9] and was thoroughly vortexed to mix. Separately, a PCR reaction mix was prepared on ice using Q5 polymerase (NEB). PCR reactions were performed using 10 μL, of ligation product as template supplemented with 0.5 μL (1 U) of Q5 polymerase, 20 μL Q5 reaction buffer, 1 mM dNTP, and water for a total reaction volume of 100 μL.

For emulsification, PCR reactions were mixed with oil at a 1:10 (PCR:oil) volumetric ratio. The PCR mix was pipetted into a cryovial tube containing emulsion oil and vortexed at maximum power using a VWR benchtop vortexer for 1 minute until a milky white emulsion formed. The emulsion was distributed as 100 μL aliquots and PCR was performed in a MJ Research PTC-200 thermocycler.

To break the emulsion post-PCR, aliquots were transferred to microcentrifuge tubes and spun for 20 minutes to separate the oil and aqueous phases. As much oil as possible was removed from the top of the biphasic solution. Then 300 μL of 2-butanol (Sigma-Aldrich 19440) was added to break the emulsion and tubes were vortexed. For reaction clean-up, 1 mL of ADB (Zymo) was added, tubes were vortexed, and PCR clean-up columns (Zymo research) were used to purify the amplicons. Purified amplicons were then visualized using agarose gel electrophoresis and cloned or further amplified with suppression PCR.

Suppression PCR to Generate Clonable Amplicons

Purified emulsion PCR products were used as a template for suppression PCR. Both emulsion primers were designed with a suppression tail of (CATCAGGTTTCATCCTGCCG-GCATGAGCGGCTAACGG; SEQ ID NO:1) so that amplicon ends form an inverted repeat. For suppression PCR, the distal-binding primer (CATCAGGTTTCATCCTGCCGG; SEQ ID NO:2) was used (30 cycles, Tm of 55° C.). PCR products were visualized on a gel and the band of the appropriate length was excised and cloned into a multiple cloning site flanked by EcoRI and BamHI.

Solubility Assay Using a Beta-Lactamase Folding Reporter

We modified pSALect to create pSALect-EB by placing EcoRI and BamHI restriction sites in between the tat signal sequence and the mature TEM-1 beta-lactamase sequence. For library creation, digested pSALect-EB vector and amplicons were ligated and purified with a PCR clean-up column (Zymo). Purified plasmids were then introduced into MC1061 derivative strains by electroporation [14]. Cells were rescued for 2 hours at 37° C. and grown overnight in 200 mL 2YT liquid media supplemented with 25 μg/mL chloramphenicol. Rescued cells were also dilution plated onto LB chloramphenicol plates for titering. A dilution equivalent of 1 μL overnight culture was then spread on LB plates supplemented with chloramphenicol (25 μg/mL) and ampicillin at different concentrations ranging from 1 to 100 μg/mL. Plates were incubated for 16 hours at 30° C. Plasmids were harvested from plates as libraries or colonies were grown overnight for plasmid isolation.

DNAseq of Libraries

Isolated plasmids were quantitated using a Nanodrop (Thermo Scientific) and fragmented using a Covaris S220 using the recommended protocols in the TruSeq kit (Illumina). The TruSeq procedure was used to prep the libraries for sequencing. Pools were prepared separately, barcoded, quantitated using a Library Quant Kit (Kapa Biosystems), combined, and sequenced on a MiSeq using a 300 cycle v2 kit.

Reads were quality trimmed and mapped to the reference sequences using BWA (0.6.1-r104). Samtools mpileup was used to extract per-base coverage and then an in-house python script and Microsoft Excel were used to normalize the data. As some inserts were partial gene fragments and also contributed to the per-base read coverage score, we took the median as the read coverage score for the entire gene. Manual inspection of the read coverage for several genes showed that the median was an acceptable measurement of whole gene read coverage. The read coverage per gene was then pool-normalized by dividing by the sum of read coverages for all genes in each pool.

Confirmation of Solubility with Western Blotting

Plasmids from the 5 µg/mL ampicillin condition were digested with EcoRI and BamHI and the 700 bp band corresponding to the library of gene inserts was gel purified and cloned into an arabinose-inducible expression vector with a C-terminal 3× FLAG tag. 72 colonies were Sanger sequenced, and 26 unique inserts were recovered. Cells were transformed with plasmid DNA and the resulting strains were grown overnight, reinoculated, induced with arabinose (0.2% w/v), and harvested after 4 hours. Cells were pelleted by centrifugation for 5 minutes at 2500 rcf, and the cell pellet was resuspended with BugBuster MasterMix (Novagen) at a ratio of 1 mL BugBuster per 0.1 g cell pellet. Cells were lysed for 20 minutes at 25° C. on a rocking platform and soluble protein was recovered by taking the supernatant after centrifugation at 12,000 rcf for 15 minutes. The insoluble fraction was resuspended in an equal amount of BugBuster. Subsequent Western blotting was performed with Monoclonal Anti-FLAG M2-HRP antibody (Sigma A8592) and ECL Western Blotting Substrate (Pierce 32106). Images were quantitated using ImageJ.

REFERENCES

1. Zhou, Kang, et al. "Enhancing solubility of deoxyxylulose phosphate pathway enzymes for microbial isoprenoid production." Microbial Cell Factories, 11.1 (2012): 148.
2. Steen, Eric J., et al. "Metabolic engineering of *Saccharomyces cerevisiae* for the production of n-butanol." Microbial Cell Factories, 7.1 (2008): 36.
3. Atsumi, Shota, et al. "Engineering the isobutanol biosynthetic pathway in *Escherichia coli* by comparison of three aldehyde reductase/alcohol dehydrogenase genes." Applied Microbiology and Biotechnology, 85.3 (2010): 651-657.
4. Yoshikuni, Yasuo, et al. "Redesigning enzymes based on adaptive evolution for optimal function in synthetic metabolic pathways." Chemistry & Biology, 15.6 (2008): 607-618.
5. Borovkov, Alex Y., et al. "High-quality gene assembly directly from unpurified mixtures of microarray-synthesized oligonucleotides." Nucleic Acids Research, 38.19 (2010): e180-e180.
6. Kosuri, Sriram, et al. "Scalable gene synthesis by selective amplification of DNA pools from high-fidelity microchips." Nature Biotechnology, 28.12 (2010): 1295-1299.
7. Xu, Qikai, et al. "Design of 240,000 orthogonal 25mer DNA barcode probes." Proceedings of the National Academy of Sciences, 106.7 (2009): 2289-2294.
8. LeProust, Emily M., et al. "Synthesis of high-quality libraries of long (150mer) oligonucleotides by a novel depurination controlled process." Nucleic Acids Research, 38.8 (2010): 2522-2540.
9. Williams, Richard, et al. "Amplification of complex gene libraries by emulsion PCR." Nature Methods, 3.7 (2006): 545-550.
10. Shagin, Dmitry A., et al. "Regulation of average length of complex PCR product." Nucleic Acids Research, 27.18 (1999): e23-i.
11. Fisher, Adam C., Woojin Kim, and Matthew P. Delisa. "Genetic selection for protein solubility enabled by the folding quality control feature of the twin-arginine translocation pathway." Protein Science, 15.3 (2006): 449-458.
12. Lim, Hyung-Kwon, et al. "Mining mammalian genomes for folding competent proteins using Tat-dependent genetic selection in *Escherichia coli*." Protein Science, 18.12 (2009): 2537-2549.
13. Ueyama, Takehiko, et al. "Sequential binding of cytosolic Phox complex to phagosomes through regulated adaptor proteins: evaluation using the novel monomeric Kusabira-Green System and live imaging of phagocytosis." The Journal of Immunology, 181.1 (2008): 629-640.
14. Kittleson, Joshua T., Sherine Cheung, and J. Christopher Anderson. "Rapid optimization of gene dosage in *E. coli* using DIAL strains." Journal of Biological Engineering, 5.10 (2011).
15. D'Angelo Sara, Velappan Nileena, et al. "Filtering" genic" open reading frames from genomic DNA samples for advanced annotation." BMC Genomics, 12.
16. Zhou, Xiaochuan, et al. "Microfluidic PicoArray synthesis of oligodeoxynucleotides and simultaneous assembling of multiple DNA sequences." Nucleic Acids Research, 32.18 (2004): 5409-5417.
17. Kim, Ikjin, et al. "High-throughput Analysis of in vivo Protein Stability." Molecular & Cellular Proteomics, 12.11 (2013): 3370-3378.
18. Waldo, Geoffrey S., et al. "Rapid protein-folding assay using green fluorescent protein." Nature Biotechnology, 17.7 (1999): 691-695.
19. Cabantous, Stephanie, Thomas C. Terwilliger, and Geoffrey S. Waldo. "Protein tagging and detection with engineered self-assembling fragments of green fluorescent protein." Nature Biotechnology, 23.1 (2004): 102-107.
20. Blakeley, Brett D., Alex M. Chapman, and Brian R. McNaughton. "Split-superpositive GFP reassembly is a fast, efficient, and robust method for detecting protein-protein interactions in vivo." Molecular BioSystems, 8.8 (2012): 2036-2040.
21. Cabantous, Stéphanie, et al. "New molecular reporters for rapid protein folding assays." PLoS One 3.6 (2008): e2387.
22. Foit, Linda, et al. "Optimizing protein stability in vivo." Molecular Cell, 36.5 (2009): 861-871.
22. Vogel, Christine, and Edward M. Marcotte. "Calculating absolute and relative protein abundance from mass spectrometry-based protein expression data." Nature Protocols, 3.9 (2008): 1444-1451.

Although the foregoing invention has been described in some detail by way of illustration and example for purposes of clarity of understanding, one of skill in the art will appreciate that certain changes and modifications may be practiced within the scope of the appended claims.

All publications, accession numbers, and patent applications cited in this specification are herein incorporated by

---

INFORMAL SEQUENCE LISTING

SEQ ID NO: 1
DNA sequence of suppression tail
CATCAGGTTTCATCCTGCCGGCATGAGCGGCTAACGG SEQ ID NO: 2
DNA sequence of suppression PCR primer
CATCAGGTTTCATCCTGCCGG

---

---

What is claimed is:

1. A method for producing simultaneously a plurality of synthetic polynucleotides from a plurality of oligonucleotides such that the synthetic polynucleotide encodes a target protein,
the method comprising:
   a) designing the plurality of oligonucleotides such that a codon of the oligonucleotide is selected based on the codon usage frequency of a host cell and an overhang region forms when the oligonucleotide anneals to another oligonucleotide in the plurality;
   b) generating the plurality of oligonucleotides;
   c) phosphorylating the plurality of oligonucleotides;
   d) performing a ligation reaction with the plurality of phosphorylated oligonucleotides to generate a plurality of nucleic acid templates; and
   e) performing a PCR reaction in a single reaction vessel to produce the plurality of synthetic polynucleotides.

2. The method of claim 1, wherein the synthetic polynucleotide is about 400 bp to about 1.5 kb.

3. The method of claim 1, wherein the synthetic polynucleotide is about 800 bp.

4. The method of claim 1, wherein each synthetic polynucleotide of the plurality is essentially the same length.

5. The method of claim 1, wherein more than one synthetic polynucleotides are produced in the reaction vessel.

6. The method of claim 5, wherein at least about 10 different synthetic polynucleotides are produced in the reaction vessel.

7. The method of claim 5, wherein at least about 100 different synthetic polynucleotides are produced in the reaction vessel.

8. The method of claim 1, wherein the plurality of synthetic polynucleotides encode a plurality of target proteins.

9. The method of claim 8, wherein the plurality of target proteins is about 10 to about 200 target proteins.

10. The method of claim 1, further comprising determining the nucleic acid sequences of the synthetic polynucleotides.

11. The method of claim 10, wherein determining the nucleic acid sequences comprises performing next-generation sequencing.

12. The method of claim 1, wherein the oligonucleotide has less than or equal to 15 nucleic acids at either the 5' end or 3' end that are identical to those of another oligonucleotide in the plurality.

13. The method of claim 1, wherein the oligonucleotide is at least about 30 bp to about 175 bp.

14. The method of claim 1, wherein the oligonucleotide is at least about 100 bp to about 175 bp.

15. The method of claim 1, wherein the codon usage frequency is the codon usage frequency of *Escherichia coli*.

16. The method of claim 1, wherein generating the plurality of oligonucleotides comprises synthesizing the oligonucleotides on a microarray.

17. The method of claim 1, wherein performing a PCR reaction comprises performing emulsion PCR and suppression PCR.

18. The method of claim 17, wherein emulsion PCR comprises an oil, a surfactant, a DNA polymerase, an aqueous buffer and dNTPs.

19. The method of claim 1, further comprising isolating the synthetic polynucleotide.

20. The method of claim 19, wherein isolating the synthetic polynucleotide comprises:
   i) introducing the synthetic polynucleotide into an expression vector to generate an expression construct;

ii) introducing the expression construct into a host cell to produce a transformed host cell;
iii) culturing the transformed host cell under conditions to promote the expression of the expression construct; and
iv) extracting the synthetic polynucleotide from the transformed host cell.

21. The method of claim 1, further comprising producing the protein encoded by the synthetic polynucleotide.

22. The method of claim 21, further comprising:
i) introducing the synthetic polynucleotide into an expression vector to generate an expression construct;
ii) introducing the expression construct into a host cell to produce a transformed host cell;
iii) culturing the transformed host cell under conditions to produce the protein encoded by the synthetic polynucleotide.

23. The method of claim 20, wherein the expression construct comprises the synthetic polynucleotide operably linked to a selectable or screenable marker gene.

24. The method of claim 23, further comprising culturing the transformed host cell under selective conditions and extracting the synthetic polynucleotide from the cell.

25. The method of claim 23, further comprising screening the transformed cell to enrich for a cell that expresses the synthetic polynucleotide and extracting the synthetic polynucleotide from the cell.

26. The method of claim 22, further comprising isolating the protein produced by the transformed host cell.

27. A system for simultaneously generating a plurality of synthetic polynucleotides in a multiplex manner, the system comprising:
a) a module for designing a plurality of oligonucleotides, wherein a codon of the oligonucleotide is selected based on the codon usage frequency of a host cell and an overhang region forms when the oligonucleotide anneals to another oligonucleotide in the plurality;
b) a module for generating a plurality of oligonucleotides;
c) a module for simultaneously synthesizing the plurality of synthetic polynucleotides in a multiplex manner and in a single reaction vessel comprising:
i) reagents for phosphorylating the plurality of oligonucleotides;
ii) reagents for ligating the plurality of phosphorylated oligonucleotides to generate a plurality of nucleic acid templates; and
iii) reagents for amplifying the nucleic acid templates to generate the plurality of synthetic polynucleotides, wherein the plurality of synthetic polynucleotides encode a plurality of proteins.

28. The system of claim 27, wherein the module for designing oligonucleotides comprises an algorithm to select oligonucleotides that have less than or equal to 15 nucleic acids at either the 5' end or 3' end that are identical to those of a selected oligonucleotide.

29. The system of claim 28, wherein the algorithm selects oligonucleotides that have an overhang region with a melting temperature of about 65° C.

30. The system of claim 28, wherein the selected oligonucleotides are at least 30 to about 175 bp.

31. The system of claim 28, wherein the selected oligonucleotides are at least 100 bp to about 175 bp.

32. The system of claim 27, wherein the codon usage frequency is the codon usage frequency of *Escherichia coli*.

33. The system of claim 27, wherein the module for generating the plurality of oligonucleotides comprises a microarray.

34. The system of claim 27, wherein the synthetic polynucleotide is about 400 bp to about 1.5 kb.

35. The system of claim 27, wherein the synthetic polynucleotide is about 800 bp.

36. The system of claim 27, wherein each synthetic polynucleotide of the plurality is the same length.

37. The system of claim 27, wherein the reagents for phosphorylating comprise a polynucleotide kinase and a buffer.

38. The system of claim 27, wherein the reagents for ligating comprise a DNA ligase and a buffer.

39. The system of claim 27, wherein the reagents for amplifying comprise an oil, a surfactant, a DNA polymerase, an aqueous buffer and dNTPs.

40. The system of claim 27, wherein the module for synthesizing further comprises a reagent for isolating the plurality of synthetic polynucleotides.

* * * * *

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: DNA sequence of suppression tail

<400> SEQUENCE: 1
catcaggttt catcctgccg gcatgagcgg ctaacgg                              37

<210> SEQ ID NO 2
<211> LENGTH: 21
<212> TYPE: DNA
<213> ORGANISM: Artificial Sequence
<220> FEATURE:
<223> OTHER INFORMATION: DNA sequence of suppression PCR primer

<400> SEQUENCE: 2
catcaggttt catcctgccg g                                              21
```